US012805724B2

(12) United States Patent
Laine et al.

(10) Patent No.: US 12,805,724 B2
(45) Date of Patent: Nov. 24, 2026

(54) METHOD FOR MAINTAINING CONNECTIVITY WITH A HOSPITAL NETWORK

(71) Applicant: GE Precision Healthcare LLC, Wauwatosa, WI (US)

(72) Inventors: Tuomas Valtteri Laine, Vantaa (FI); Matthew Richard Pekarske, Grafton, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 968 days.

(21) Appl. No.: 17/651,048

(22) Filed: Feb. 14, 2022

(65) Prior Publication Data

US 2023/0255485 A1 Aug. 17, 2023

(51) Int. Cl.

| | |
|---|---|
| ***A61B 5/00*** | (2006.01) |
| ***H04L 1/00*** | (2006.01) |
| ***H04W 4/23*** | (2018.01) |
| *H04W 84/12* | (2009.01) |

(52) U.S. Cl.

CPC .......... *A61B 5/0022* (2013.01); *A61B 5/0024* (2013.01); *H04L 1/0025* (2013.01); *H04W 4/23* (2018.02); *H04W 84/12* (2013.01)

(58) Field of Classification Search

CPC ..... A61B 5/0022; A61B 5/0024; A61B 5/746; A61B 5/021; A61B 5/747; H04L 1/0025; H04W 4/23; H04W 84/12; H04W 88/04

See application file for complete search history.

(56) References Cited

U.S. PATENT DOCUMENTS

| | | | |
|---|---|---|---|
| 7,574,208 | B2 | 8/2009 | Hanson et al. |
| 7,616,110 | B2 | 11/2009 | Crump et al. |
| 7,633,952 | B2 | 12/2009 | Ong et al. |
| 7,715,795 | B2 | 5/2010 | Pirzada et al. |
| 8,340,117 | B2 | 12/2012 | Capone et al. |
| 8,509,159 | B2 | 8/2013 | Shao et al. |
| 10,159,020 | B2 | 12/2018 | Schmitt |
| 2007/0058657 | A1 | 3/2007 | Holt et al. |

(Continued)

FOREIGN PATENT DOCUMENTS

WO WO-2016099844 A1 * 6/2016 ............. G16H 40/67

*Primary Examiner* — Sujoy K Kundu
*Assistant Examiner* — Raul Rivas
(74) *Attorney, Agent, or Firm* — McCoy Russell LLP

(57) ABSTRACT

Methods and systems are provided for forwarding information from a patient monitoring device not connected to the wireless network to a wireless network of a healthcare facility, using out-of-band (OOB) radio communication. In one embodiment, a method for a patient monitoring device includes initiating a connectionless communication forwarding mode with a neighboring wireless device of the patient monitoring device via out-of-band (OOB) radio communication, the patient monitoring device not connected to a wireless local area network (WLAN) of the healthcare facility and the neighboring wireless device connected to the WLAN; and while operating in the connectionless communication forwarding mode, transmitting data to an information system of the healthcare facility connected to the WLAN, the data transmitted to the neighboring wireless device via the OOB radio communication, and forwarded to the information system by the neighboring wireless device via the WLAN.

8 Claims, 4 Drawing Sheets

(56) References Cited

U.S. PATENT DOCUMENTS

| | | | | |
|---|---|---|---|---|
| 2013/0172042 | A1* | 7/2013 | Kim | H04W 76/10<br>455/524 |
| 2016/0165387 | A1* | 6/2016 | Nhu | H04W 4/80<br>455/41.1 |
| 2017/0143206 | A1* | 5/2017 | Kotz | G08C 17/02 |
| 2017/0155427 | A1 | 6/2017 | Hasan et al. | |
| 2017/0223490 | A1* | 8/2017 | Baker | A61B 5/002 |
| 2018/0227800 | A1* | 8/2018 | Wang | H04W 28/082 |
| 2019/0209022 | A1* | 7/2019 | Sobol | A61B 5/681 |
| 2022/0215944 | A1* | 7/2022 | Al-Ali | G16H 40/63 |

* cited by examiner

METHOD FOR MAINTAINING CONNECTIVITY WITH A HOSPITAL NETWORK

TECHNICAL FIELD

Embodiments of the subject matter disclosed herein relate generally to wireless communications, and in particular to wireless patient monitoring systems.

BACKGROUND

A wireless local area network (WLAN) may be used in a hospital environment to transmit and receive information among elements of the network. Mobile clients such as wireless handheld devices may be wirelessly connected to the network via a plurality of access points (AP) of the WLAN. Information may be transmitted between the handheld devices and the network via the APs, such that data of hospital information systems may be accessed by the mobile clients. The mobile clients may include patient monitoring devices or software used by caregivers to remotely monitor patients as the patients move around the hospital environment.

Connection loss in an enterprise WLAN environment, such as a hospital, can happen due to various reasons. A mobile client may move outside of a range of a connected AP, or there may be noise or interference on a channel of the AP. For example, the mobile client may be operating in a wireless environment where radio frequency (RF) propagation is challenging, for example, due to thick walls or obstacles. A radio protocol or software of the mobile client or the AP may also be unstable. When the mobile client loses a connection to the network, information transmitted to the mobile client over the network may not be received at the mobile client. The information may include time sensitive data, such as a change in a status of a patient. For example, a clinical alarm may be sent to a caregiver to urgently attend to a patient. If the information is not received in a timely manner, the ability of the caregiver to provide adequate care for the patient may be affected.

SUMMARY

The current disclosure at least partially addresses one or more of the above identified issues by a method for a patient monitoring device of a healthcare facility, the method comprising initiating a connectionless communication forwarding mode with a neighboring wireless device of the patient monitoring device via out-of-band (OOB) radio communication, the patient monitoring device not being connected to a wireless local area network (WLAN) of the healthcare facility and the neighboring wireless device being connected to the WLAN; and while operating in the connectionless communication forwarding mode, transmitting data to an information system of the healthcare facility that is connected to the WLAN, the information being transmitted to the neighboring wireless device via the OOB radio communication, and being forwarded to the information system by the neighboring wireless device via the WLAN.

In this way, the OOB radio communication may be used to relay messages and/or information between a device that is not connected to the WLAN and a device that is connected to the WLAN. The OOB radio communication may be connectionless and unidirectional, and may rely on short-range, low-power radio signals, such as within a Medical Body Area Network (MBAN). By relaying the messages and/or information through the device connected to the WLAN, the device not connected to the WLAN may continue to transmit information to other connected devices and/or information systems of the healthcare facility over the WLAN, thereby ensuring that time-sensitive data such as patient status information, patient data, alerts, notifications, and/or other types of data are received by a caregiver (e.g., via a viewing device) in a timely manner. By ensuring that the time-sensitive data is received in a timely manner, the quality of patient care may be increased and the likelihood of an undesirable outcome for a patient may be reduced.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
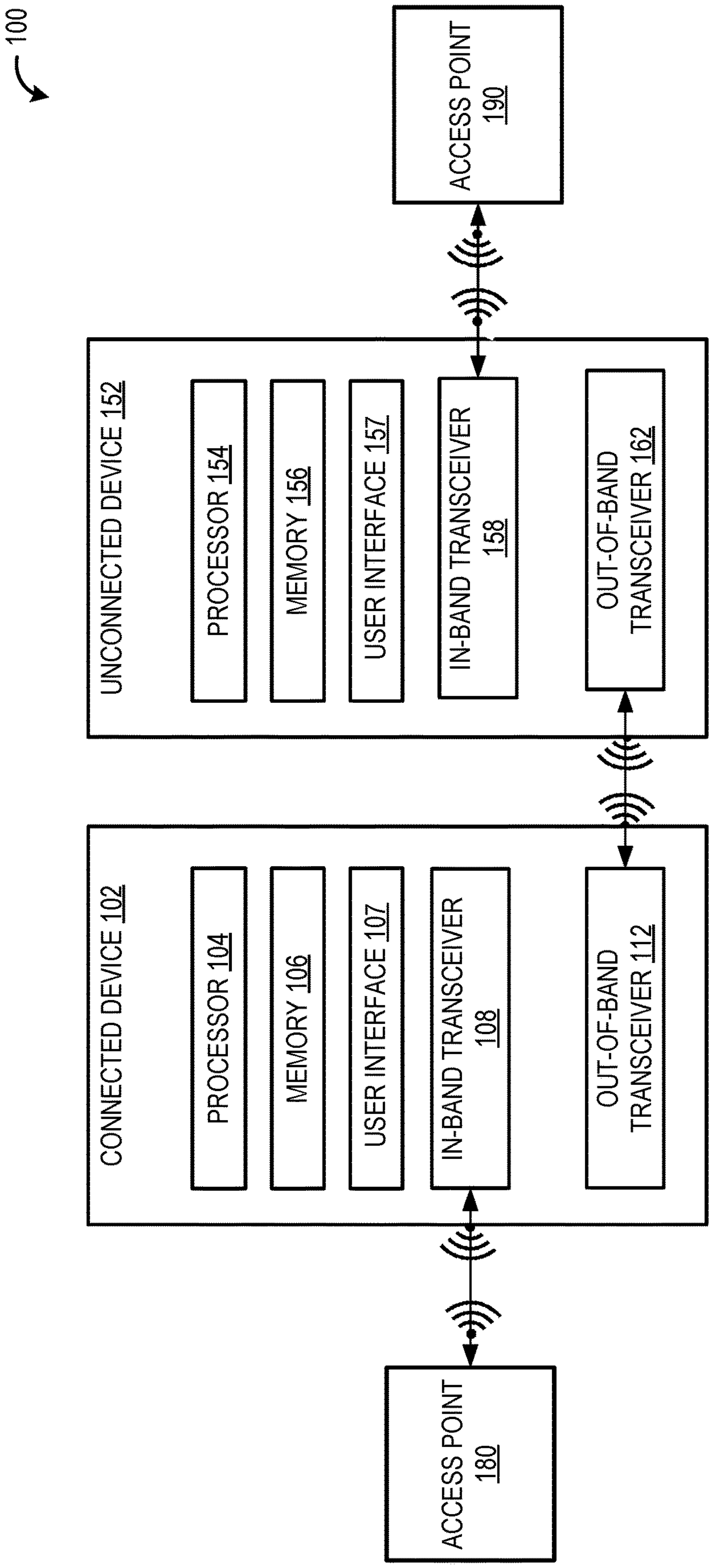
FIG. 1 is a schematic block diagram of a wireless system including a connected wireless device and an unconnected device, in accordance with one or more embodiments of the present disclosure.

In a hospital or healthcare facility, monitoring of a patient's physiological information may be accomplished in part using wireless patient monitors or other mobile medical devices. For example, a patient may be physically connected (e.g., via one or more sensors) to one or more hospital information systems including a wireless local area network (WLAN, also referred to herein as the wireless network or the network). As the patient and/or a caregiver of the patient move about the hospital, the caregiver may monitor (or view) the patient data and status at a central viewer which receives the patient data and status from the network from a wireless patient monitoring device placed at the patient. Monitoring the patient may include receiving data from the wireless patient monitoring device (e.g., patient data, physiological data, alerts, messages, notifications, etc.) at a wireless device of the caregiver. Monitoring the patient may also include uploading data to hospital information systems via the wireless network (e.g., inputting new patient data collected by the caregiver). The wireless patient monitoring device may be connected to the wireless network via at least one of a plurality of APs. The wireless network may further include a patient information database and/or other devices by which medical professionals may access and monitor patient data.

As the patient moves about the hospital or healthcare facility, a strength of an available wireless signal may change, for example, as the wireless patient monitoring device moves closer to or further from an AP that the wireless patient monitoring device is connected to (also referred to herein as the connected AP). The signal strength may affect a speed of information transmission, energy used for transmission, and a time between information transmission by the wireless patient monitoring device and receipt of the information by the network.

However, in some cases, a connection between the WLAN client and a connected AP may be lost, and no other APs may be available to connect to, whereby the WLAN client may not be able to connect to the network. When this occurs, information may not be delivered to a recipient in a timely manner. For example, in a medical environment, information such as actionable patient status information may not be delivered to a caregiver in a timely manner. To support the timely delivery of the information such as the patient status information when network connectivity is not available, methods and systems are provided herein for the WLAN client to deliver the information through an alternative route using an out-of-band (OOB) communication method within a collaborative networked system. The OOB communication method may be used to send information (e.g., patient status information) to neighboring wireless clients connected to the network during network connection loss. The information may include, for example, clinical or technical alarms. The information may be transmitted to the neighboring wireless clients in unidirectional and connectionless manner. Similarly, a caregiver may input information into the WLAN client when the WLAN client is not connected to the network, and the information may be transmitted via the OOB communication to a receiving neighboring wireless client connected to the network. The receiving neighboring wireless client may then forward the information to a hospital information system via the network.

Figure 2A:
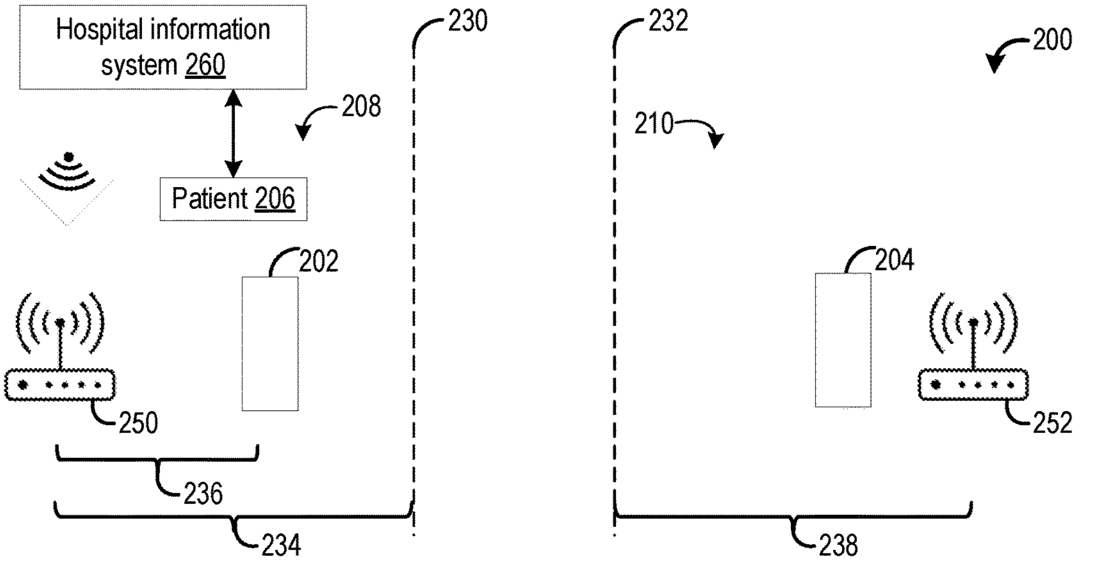
FIG. 2A is a diagram showing two wireless devices of wireless system in a hospital environment in a first configuration, in accordance with one or more embodiments of the present disclosure.
Figure 2B:
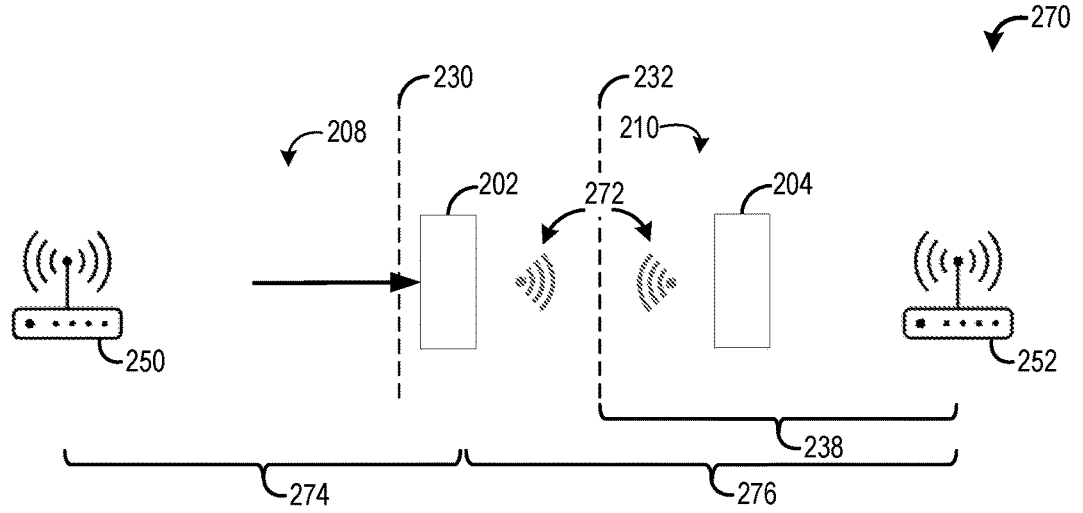
FIG. 2B is a diagram showing two wireless devices of wireless system in a hospital environment in a second configuration, in accordance with one or more embodiments of the present disclosure.
Figure 2C:
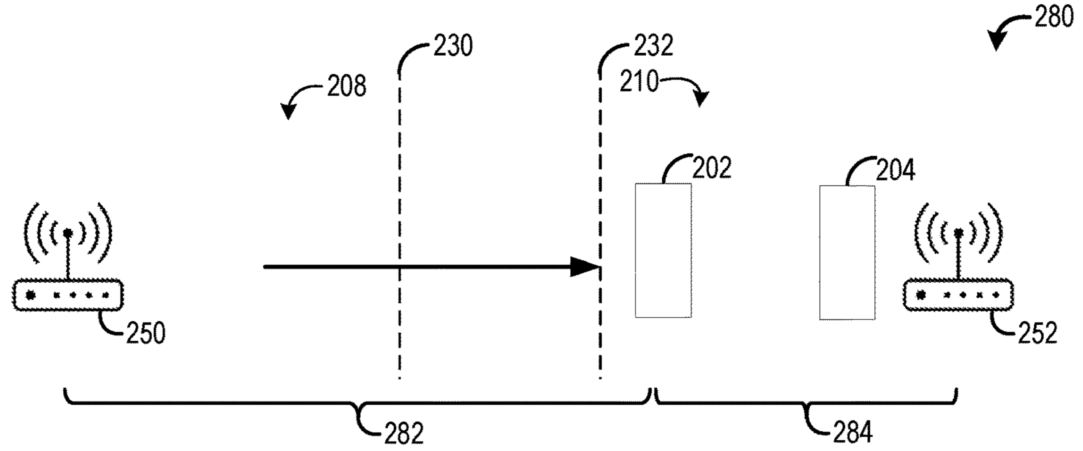
FIG. 2C is a diagram showing two wireless devices of wireless system in a hospital environment in a third configuration, in accordance with one or more embodiments of the present disclosure.

FIG. 1 shows a wireless system, comprising a wireless device connected to a WLAN and an unconnected wireless device. The connected device and the unconnected device may be wireless patient monitoring devices in different states of connectivity to different access points of a hospital network, as shown in FIGS. 2A, 2B, and 2C. While two wireless patient monitoring devices are depicted in FIGS. 2A, 2B, and 2C, in various embodiments, either one of the depicted wireless patient monitoring devices may alternatively be wireless device of a remote caregiver, or a different wireless device of the wireless system. FIG. 2A shows two wireless patient monitoring devices connected to the hospital network in a first configuration at a first time, where a first wireless patient monitoring device is connected to a first AP of the hospital network, and a second wireless patient monitoring device is connected to a second AP of the hospital network. FIG. 2B shows the two wireless patient monitoring devices in a second configuration at a second time, where the first wireless patient monitoring device has lost a connection to the first AP, and the second wireless patient monitoring device is connected to the second AP of the hospital network. The two wireless patient monitors may each include a radio communication module, which may be used for out-of-band (OOB) communications. Upon losing the first connection to the first AP, the first wireless patient monitoring device may scan for a neighboring wireless device, such as the second wireless patient monitoring device, via the OOB communications. The second wireless patient monitoring device may advertise its availability for message forwarding via the OOB communications by following one or more steps of a method described in FIG. 3. If the first wireless patient monitoring device establishes the OOB communications with the second wireless patient monitoring device, the first wireless patient monitoring device may forward information such as patient status data to the second wireless patient monitoring device, by following one or more steps of a method described in FIG. 4. FIG. 2C shows the two wireless patient monitoring devices connected to the hospital network in a third configuration at a third time, where the first wireless patient monitoring device and the second wireless patient monitoring device are both connected to the second AP of the hospital network, and the message forwarding via the OOB communications is no longer relied on.

Referring now to FIG. 1, an exemplary wireless system 100 is shown, including a connected device 102 and an unconnected device 152, where connected device 102 is connected to a wireless network (not shown in FIG. 1) of wireless system 100. In various embodiments, wireless system 100 may be established within a hospital environment. Connected device 102 and unconnected device 152 may be of a same type of device, or connected device 102 and unconnected device 152 may be different types of devices. For example, connected device 102 may be a first patient monitoring device for monitoring a first type of patient, and unconnected device 152 may be a second patient monitoring device for monitoring a second type of patient. In various embodiments, unconnected device 152 may be a wireless patient monitoring device placed on or at a patient, and connected device 102 may be a wireless device of a caregiver such as a cell phone located in a proximity of the patient. Either of the caregiver and the patient may move around the hospital environment, such that the caregiver and the patient, and therefore the connected device 102 and the unconnected device 152, may at times be in close proximity, and other times may not be in close proximity.

Connected device 102 may include a processor 104. Processor 104 may control the operation of connected device 102 in response to control signals from a user interface (UI) 107. In some embodiments, UI 107 is integrated into connected device 102, where a user may interact with, adjust, or select control elements in the UI 107 (e.g., buttons, knobs, touchscreen elements, etc.) to send one or more control signals to processor 104 from UI 107. In other embodiments, UI 107 is not integrated into connected device 102, and the user may interact with, adjust, or select control elements in UI 107 via a user input device, such as a mouse, track ball, touchpad, etc., or the operator may interact with UI 107 via a separate touchscreen, where the operator touches a display screen of UI 107 to interact with UI 107, or via another type of input device.

Processor 104 may execute instructions stored on a memory 106 to control connected device 102. As discussed herein, the memory 106 may include any non-transitory computer readable medium in which programming instructions are stored. For the purposes of this disclosure, the term "tangible computer readable medium" is expressly defined to include any type of computer readable storage. The example methods and systems may be implemented using coded instruction (e.g., computer readable instructions) stored on a non-transitory computer readable medium such as a flash memory, a read-only memory (ROM), a random-access memory (RAM), a cache, or any other storage media in which information is stored for any duration (e.g. for extended period time periods, permanently, brief instances, for temporarily buffering, and/or for caching of the information). Computer memory of computer readable storage mediums as referenced herein may include volatile and non-volatile or removable and non-removable media for a storage of electronic-formatted information such as computer readable program instructions or modules of computer readable program instructions, data, etc. that may be standalone or as part of a computing device. Examples of computer memory may include any other medium which can be used to store the desired electronic format of information and which can be accessed by the processor or processors or at least a portion of a computing device. In various embodiments, the memory 106 may include an SD memory card, an internal and/or external hard disk, USB memory device, or similar modular memory.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Connected device 102 may include an in-band transceiver 108. In various embodiments, in-band transceiver 108 may be or may include a WLAN wireless card. In some embodiments, the WLAN card may be an original equipment manufacturer (OEM) card, and may include a storage medium having computer executable code and a processor to execute that code, thus effectuating the operation of the WLAN card.

Connected device 102 may use in-band transceiver 108 to connect to the network via an AP 180. AP 180 may have a transmitter and a receiver, or a transmitter/receiver (e.g., a single device with transmitting and receiving capabilities). In various embodiments, AP 180 may be an AP that is in closest proximity to connected device 102 and/or an AP with a strongest signal in comparison to other alternative APs in a wireless environment of connected device 102.

As an example, in the hospital environment, AP 180 may be arranged at a location of the hospital environment, for example, in proximity to patients being monitored at a care unit. The network may receive wirelessly transmitted information from AP 180, and relay the information to a hospital information system suitable for collecting and managing such information. For example, connected device 102 may be a wireless patient monitoring device that is communicating wirelessly with AP 180, and relaying physiological information collected by the wireless patient monitoring device through AP 180 to the hospital information system via the network. Connected device 102 may utilize in-band transceiver 108 and a transceiver of AP 180 to facilitate the wireless transmission of the physiological data.

Unconnected device 152 is a similar device to connected device 102, and as such, includes components of connected device 102 described above, such as a processor 154, a memory 156, user interface 157, an in-band transceiver 158. Similar to connected device 102, unconnected device 152 may use in-band transceiver 158 to connect to the network via an AP 190. In various embodiments, the AP 190 may be an AP that is in closest proximity to unconnected device 152 and/or an AP with a strongest signal in comparison to alternative APs of a wireless environment of unconnected device 152.

In various embodiments, AP 180 and AP 190 may be different APs that are placed at different locations within the wireless environment. For example, AP 180 may be placed in a first unit of a hospital, to allow caregivers of the first unit access to the network, and AP 190 may be placed in a second unit of the hospital, to allow caregivers of the second unit access to the network. The first unit may be next to or in close proximity to the second unit. If the first unit is next to the second unit, and connected device 102 is in the first unit, connected device 102 may be able to connect to both AP 180 and AP 190. However, an RSSI of AP 180 may be stronger than an RSSI of AP 190, whereby connected device 102 may establish a connection with AP 180, with AP 190 thus being an alternative AP.

Alternatively, the first unit may not be next to or in close proximity to the second unit. If the first unit is not next to the second unit, and connected device 102 is in the first unit, connected device 102 may be able to connect to AP 180 and may not be able to connect with AP 190. Similarly, if unconnected device 152 is in the second unit, unconnected device 152 may be able to connect to AP 190, and may not be able to connect to AP 180.

While roaming, unconnected device 152 may leave the second unit. If a distance between unconnected device 152 and AP 190 increases above a threshold distance (e.g., a roaming trigger distance), unconnected device 152 may lose a connection with AP 190. In some situations, after losing the connection with AP 190, unconnected device 152 may not be close enough to a different AP (e.g., such as AP 180) to establish a connection with the different AP. When this occurs, unconnected device 152 may not be able to send and/or receive information to and/or from the network, until unconnected device is able to establish the connection with the different AP.

Connected device 102 may include an out-of-band (OOB) transceiver 112, and unconnected device 152 may include an OOB transceiver 162. Via OOB transceiver 112, connected device 102 may communicate with OOB transceiver 162 of unconnected device 152 via OOB radio communication over an OOB communication channel. The OOB radio communication may be short-range, low-power radio communication on an allocated portion of radio frequency spectrum outside the standard Wi-Fi spectrum. For the purposes of this disclosure, the short-range, low-power radio communication may refer to communication via a low-power transmitter (e.g., 1-25 mW of effective radiated power (ERP)) with a range of a five to twenty meters. The short-range, low-power communication may rely on technologies including Bluetooth®, near-field communication (NFC), ultra-wideband (UWB), and IEEE 802.15.4. In various embodiments, the OOB channel may be a radio frequency channel within the 2360-2500 MHz band used for MBAN communication. The OOB radio communication over the OOB channel may be connectionless and unidirectional.

Via OOB transceiver 112, connected device 102 may advertise an availability for forwarding messages using the OOB radio communication. For example, connected device 102 may advertise that connected device 102 may be used to forward network traffic to the network via an OOB communication channel between connected device 102 and an unconnected device such as unconnected device 152. Forwarding network traffic via the OOB communication channel may be implemented if unconnected device 152 loses a connection with the network. An example advertising procedure which may be implemented by the connected device 102 is described in further detail below in reference to FIG. 3.

When unconnected device 152 loses the connection with the network, unconnected device 152 may detect the availability of connected device 102 for forwarding information to and from the network. Unconnected device 152 may initiate a connectionless communication forwarding mode with connected device 102 to forward the information to and from the network, as described in greater detail below. For the purposes of this disclosure, connectionless communication forwarding may refer to the relaying of data between an unconnected wireless device and a wireless network and by a connected wireless device, where a connection is not established between the unconnected wireless device and the connected wireless device. For example, when unconnected device 152 loses connectivity with the network, unconnected device 152 may not transmit a clinical or technical alarm via a WLAN connection (e.g., via in-band transceiver 158). However, the clinical or technical alarm may be relayed from unconnected device 152 to connected device 102, which may be connected to the network (e.g., via AP 180). The clinical or technical alarm may be relayed to connected device 102 over an OOB communication channel, from OOB transceiver 162 to OOB transceiver 112. Relaying of data over the OOB communication channel is described in greater detail below in reference to FIGS. 2A-4.

FIG. 2A shows a first configuration of a hospital wireless system 200 for monitoring patients in a healthcare facility, at a first time. Hospital wireless system 200 may include a first patient monitoring device 202 and a second patient monitoring device 204. First patient monitoring device 202, second patient monitoring device 204, and hospital wireless system 200 may be non-limiting embodiments of unconnected device 152, connected device 102, and wireless system 100, where either or both of first patient monitoring device 202 and second patient monitoring device 204 may be a non-limiting embodiment of either connected device 102 or unconnected device 152. First patient monitoring device 202 and second patient monitoring device 204 may be used to transmit patient physiological data of one or more patients within the hospital environment. Alternatively, in some embodiments, one or both of first patient monitoring device 202 and second patient monitoring device 204 may be cell phones or a different type of wireless device, such as a tablet, and may not be patient monitoring devices. For example, first patient monitoring device 202 may be a patient monitoring device and second patient monitoring device 204 may be a cell phone of a caregiver, or first patient monitoring device 202 may be a cell phone of a caregiver and second patient monitoring device 204 may be a patient monitoring device.

First patient monitoring device 202 may be used by a first caregiver to monitor a patient 206 connected to a hospital information system 260. Patient monitoring device 202 may be wirelessly connected to hospital information system 260 over the network via a first AP 250 connected to a WLAN of hospital wireless system 200. Hospital information system 260 may include patient monitoring data. The patient monitoring data may include, for example, vital signs, blood pressure, and/or other physiological data. The patient monitoring data may be collected, for example, via one or more electronic sensors to which patient 206 is connected (e.g., at a bed of the healthcare facility).

Patient 206 may be receiving treatment at a first location 208 within the hospital environment. First patient monitoring device 202 may be placed on the patient at first location 208, to be used by a first caregiver remotely monitoring the patient. First patient monitoring device 202 may be wirelessly connected to the network via first AP 250 at first location 208. Second patient monitoring device 204 may be used by a second caregiver at a second location 210 including a second AP 252, and second patient monitoring device 204 may be wirelessly connected to the hospital information system 260 over the network via the second AP 252.

First patient monitoring device 202 and second patient monitoring device 204 may be mobile, and as such, first patient monitoring device 202 and/or second patient monitoring device 204 may move through areas of the healthcare facility. As they move, a connection with the connected AP may be lost (e.g., where a signal strength of a first AP may decrease below a threshold signal strength), and a new AP to which the first patient monitoring device 202 and/or second patient monitoring device 204 may switch may not be detected. As a result of not detecting the new AP, the first patient monitoring device 202 and/or second patient monitoring device 204 may not be connected to the network.

For example, first patient monitoring device 202 may be separated from AP 250 by a distance 236. At distance 236, a signal strength of AP 250 at first patient monitoring device 202 may be strong. As patient 208 is moved, first patient monitoring device 202 may move from first location 208 towards second location 210. As first patient monitoring device 202 moves towards second location 210, distance 236 between first patient monitoring device 202 and AP 250 may increase. As first patient monitoring device 202 leaves first location 208, first patient monitoring device 202 may reach a distance 234 at which the signal strength of AP 250 at first patient monitoring device 202 decreases below a threshold signal strength whereby first patient monitoring device 202 may lose its connection with AP 250. A dashed line 230 indicates a boundary of a range of AP 250, where if first patient monitoring device 202 is within the boundary (e.g., if distance 236 is less than distance 234), first patient monitoring device 202 may be connected to AP 250, and if first patient monitoring device 202 is outside the boundary (e.g., if distance 236 is greater than distance 234), first patient monitoring device 202 may not be connected to AP 250. Similarly, a dashed line 232 indicates a boundary of a range of AP 252, at a distance 238 from AP 252, where if second patient monitoring device 204 is within the boundary, second patient monitoring device 204 may be connected to AP 252, and if second patient monitoring device 204 is outside the boundary, second patient monitoring device 204 may not be connected to AP 250.

FIG. 2B shows a second configuration 270 of hospital wireless system 200 at a second, later time, where a position of first patient monitoring device 202 is outside the boundary indicated by dashed line 230, where the signal strength of AP 250 has decreased below the threshold signal strength, and the connection between first patient monitoring device 202 and AP 250 may not be sufficiently strong for data to be transferred reliably between first patient monitoring device 202 and AP 250. As a result of the connection not being sufficiently strong, first patient monitoring device 202 may lose connectivity with the network.

However, first patient monitoring device 202 may be separated from AP 252 by a distance 276, which may be greater than distance 238. As such, first patient monitoring device 202 may be outside the boundary of the range of AP 252 indicated by dashed line 232. Thus, first patient monitoring device 202 may not be able to connect to AP 252. Further, first patient monitoring device 202 may not detect a suitable AP in the wireless environment to connect to. For example, moving from first location 208 to second location 210 may include navigating through an area without connectivity to the network, due to a presence of obstacles such as heavy walls. As a result of not detecting a suitable AP to connect to, first patient monitoring device 202 may not be connected to the network.

As a result of not being connected to the network, first patient monitoring device 202 may search for neighboring wireless devices within a range at which first patient monitoring device 202 may communicate with the neighboring wireless devices via an OOB communication channel. First patient monitoring device 202 may detect second patient monitoring device 204, which may be advertising an availability of second patient monitoring device 204 for message forwarding to the network. In order to continue to transmit information to the network without being connected to an AP of the network, first patient monitoring device 202 may relay the information to second patient monitoring device 204 via an OOB communication channel 272, to be forwarded on to the network. For example, OOB communication channel 272 may be established between a first OOB transceiver (e.g., OOB transceiver 112 of FIG. 1) of first patient monitoring device 202 and a second OOB transceiver (e.g., OOB transceiver 162 of FIG. 1) of second patient monitoring device 204. Relaying of the information is described in greater detail below in reference to FIGS. 3 and 4.

FIG. 2C shows a third configuration 280 of hospital wireless system 200 at a third, later time, after first patient monitoring device 202 has entered second location 210. In third configuration 280, first patient monitoring device 202 is separated from AP 252 by a distance 284. At distance 284, first patient monitoring device 202 is positioned inside the boundary indicated by dashed line 232, where a signal strength of AP 252 is above a threshold signal strength for connecting with AP 252. As a result of being inside the boundary, first patient monitoring device 202 may connect to the network via AP 252. After first patient monitoring device 202 is connected to the network via AP 252, first patient monitoring device 202 may terminate the OOB radio communication over OOB communication channel 272, and subsequently may send information to the network via AP 252.

Figure 3:
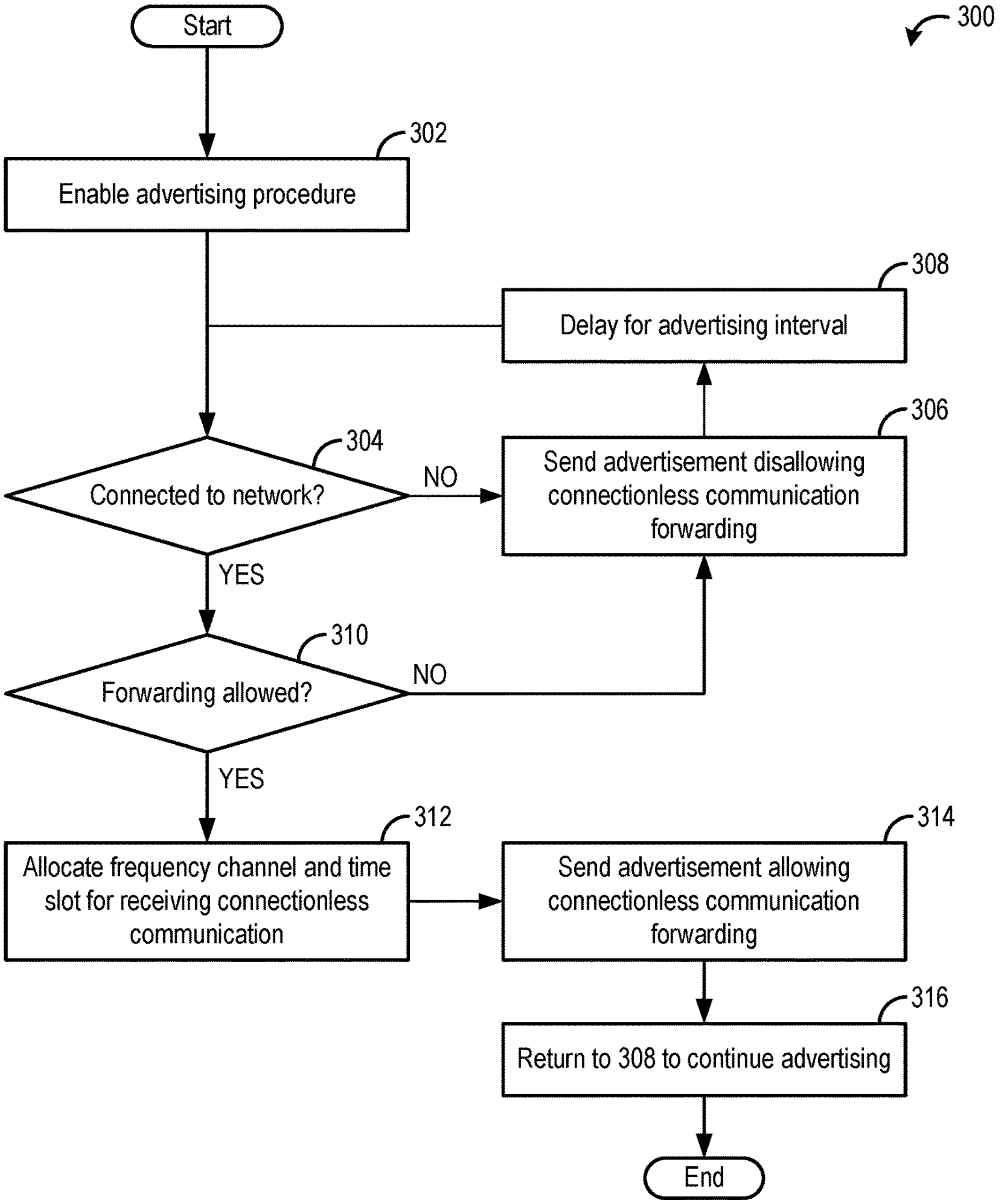
FIG. 3 is a flowchart illustrating an exemplary method for a wireless device for advertising an availability for message forwarding via an OOB communication channel, in accordance with one or more embodiments of the present disclosure.

Referring now to FIG. 3, an exemplary method 300 is shown for advertising (e.g., indicating) an availability of a first wireless device connected to a wireless network of a healthcare facility for connectionless communication forwarding from a second wireless device not connected to the wireless network. As described above, connectionless communication forwarding may refer to the relaying of data from an unconnected wireless device to a wireless network by a connected wireless device, where a connection is not established between the unconnected wireless device and the connected wireless device. In various embodiments, one or both of the first wireless device and the second wireless device may be a patient monitoring device of a healthcare facility. For example, the first wireless device may be a cell phone of a first caregiver of the healthcare facility, and the second wireless device may be a wireless patient monitoring device placed on a patient of a second caregiver of the healthcare facility.

As described above, the second wireless device may lose a connection to an AP to which the second wireless device is connected (e.g., its connected AP). When the second wireless device loses the connection to its connected AP, messages transmitted from the second wireless device to the wireless network may be relayed to the first wireless device over an OOB communication channel to be forwarded to the network (e.g., to an information system and/or or other wireless devices on the network), as described in greater detail below in reference to FIG. 4.

Method 300 and other methods described herein are described with reference to a wireless system, such as wireless system 100 of FIG. 1 and/or hospital wireless system 200 of FIGS. 2A-C. Method 300 and other methods described herein may be implemented via computer-readable instructions stored in a memory of the first wireless device, and executed by a processor of the first wireless device, such as memory 106 and processor 104 of connected device 102 of FIG. 1. The first wireless device may be a non-limiting embodiment of connected device 102 of FIG. 1 and/or second patient monitoring device 204 of FIGS. 2A-C. The second wireless device may be a non-limiting embodiment of unconnected device 152 of FIG. 1 and/or first patient monitoring device 202 of FIGS. 2A-2C.

Method 300 begins at 302, where method 300 includes enabling an advertising procedure. Enabling the advertising procedure may include determining whether the first wireless device is available to send and receive information via an OOB communication channel (e.g., OOB communication channel 272 of FIG. 2B). For example, if the first wireless device does not have an OOB transceiver (e.g., OOB transceiver 112 of FIG. 1), the first wireless device may not be available to send and receive information via the OOB communication channel. If the first wireless device has an OOB transceiver, determining whether the first wireless device is available to send and receive information via the OOB communication channel may include determining whether the OOB transceiver is functioning properly. In some cases, sending and receiving information via the OOB transceiver may be administratively disabled by a user, or disabled due to performance limitations (e.g., a limited battery life).

At 304, method 300 includes determining whether the first wireless device is connected to the wireless network. If at 304 it is determined that the first wireless device is not connected to the wireless network, method 300 proceeds to 306. At 306, method 300 includes sending an advertisement disallowing connectionless communication forwarding. By sending the advertisement disallowing the connectionless communication forwarding, the first wireless device notifies neighboring wireless devices that the first wireless device may not be able to forward information from devices not connected to the wireless network to a device on the network (e.g., a hospital information system, or a different wireless device).

In various embodiments, sending the advertisement disallowing connectionless communication forwarding may include transmitting a continuous radio signal (e.g., a beacon) over one or more OOB communication channels. For example, a pre-established OOB communication channel may be used for sending the beacon, or the beacon may be transmitted on a plurality of OOB communication channels. The beacon may include an identifier (e.g., a number, or an alphanumeric code). In some embodiments, the identifier may be a pre-established code that indicates that the first wireless device is not available for engaging in connectionless communication forwarding. A neighboring wireless device listening on the one or more OOB communication channels may receive the beacon, and decode the beacon to detect the lack of availability of the first wireless device. In other embodiments, the identifier may be linked to a cloud-based lookup service of the healthcare facility, where the neighboring wireless device listening on the one or more OOB communication channels may consult the cloud-based lookup service to decode a portion of the identifier that indicates the lack availability of the first wireless device.

At 308, after sending the advertisement disallowing the connectionless communication forwarding, method 300 includes delaying for an advertising interval before proceeding back to 304 to recheck for network connectivity. For example, the advertising interval may be between ten milliseconds and several seconds, depending on a technology used (e.g., MBAN, BLE, etc.).

If at 304 it is determined that the first wireless device is connected to the wireless network, method 300 proceeds to 310. At 310, method 300 includes determining whether connectionless communication forwarding is allowed at the first wireless device. For example, connectionless communication forwarding may not be allowed if the first wireless device is already supporting an OOB communication link, or has run out of available OOB capacity. Alternatively, the first wireless device may be serving a critical application that cannot be interrupted or slowed down by another process supporting the OOB communication link.

If at 310 it is determined that forwarding is not allowed, method 300 proceeds back to 306, where an advertisement is sent disallowing connectionless communication forwarding as described above. Alternatively, if at 310 it is determined that connectionless communication forwarding is allowed, method 300 proceeds to 312.

At 312, method 300 includes allocating a frequency channel and time slot for receiving connectionless communication. A time slot may be allocated for periodic receipt of messages from the wireless network and/or from a neighboring wireless device, where messages may be received during the time slot, and messages may not be received outside of the time slot.

For example, an MBAN may rely on time slot-based communication to send physiological data to the first wireless device from one or more wireless sensors arranged on a patient. Various time slots may be available, where time slot capacity may be limited by an MBAN communication channel used. If the MBAN communication channel has free time slots (i.e., additional capacity to spare), the MBAN channel may also be used to support OOB communication between the first wireless device and another wireless device. In other embodiments, a PAN or BAN (personal or body area network) channel may be used for short range communications.

At 314, method 300 includes sending an advertisement allowing connectionless communication forwarding. By sending the advertisement allowing connectionless communication forwarding, the first wireless device indicates to the neighboring wireless devices an availability of the first wireless device for relaying information from a neighboring wireless device that is not connected to the wireless network to one or more destinations on the network.

In various embodiments, sending the advertisement allowing connectionless communication forwarding may include transmitting a beacon over one or more OOB communication channels. As described above, the beacon may include an identifier, which may be a pre-established code that indicates the availability of the first wireless device for engaging in connectionless communication forwarding. A neighboring wireless device listening on the one or more OOB communication channels may receive the beacon, and decode the beacon to detect the availability of the first wireless device. In other embodiments, the identifier may be linked to a cloud-based lookup service of the healthcare facility, where the neighboring wireless device listening on the one or more OOB communication channels may consult the cloud-based lookup service to decode a portion of the identifier that indicates the availability of the first wireless device.

At 316, method 300 includes returning to step 308 to continue advertising. It should be appreciated that in various embodiments, method 300 may be performed iteratively or repeatedly while the first wireless device is in operation. In other words, the first wireless device may continuously advertise its availability to relay information.

Thus, if a first wireless device loses a connection with a connected AP of the network, the first wireless device may search for a second wireless device that is advertising an availability for connectionless communication forwarding as described in method 300. Once the first wireless device detects the second wireless device, the first wireless device may initiate a connectionless communication forwarding mode with the second wireless device to continue to send data to the network, as described below in reference to FIG. 4.

Figure 4:
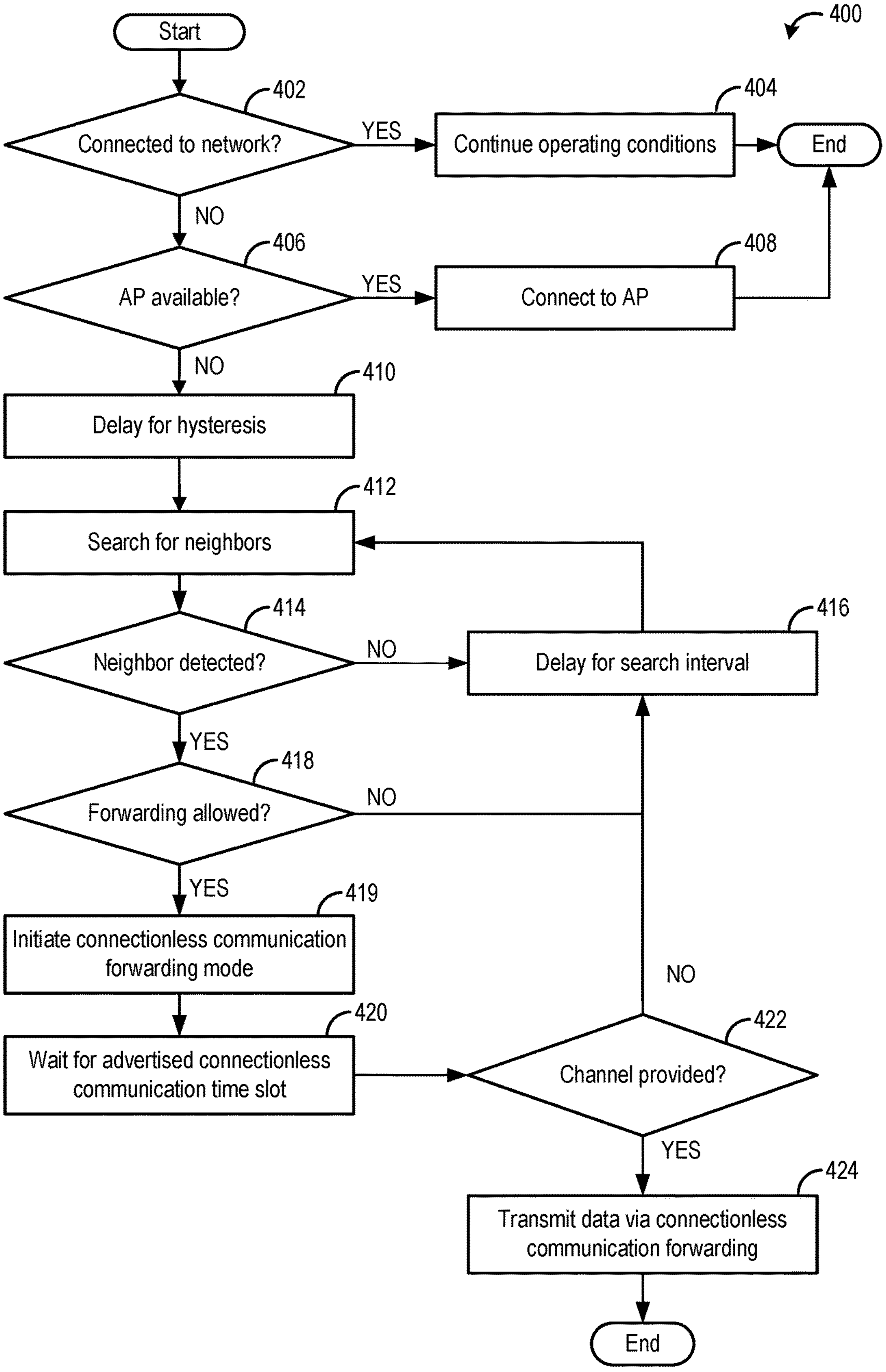
FIG. 4 is a flowchart illustrating an exemplary method for message forwarding between a two wireless devices via an OOB communication channel, in accordance with one or more embodiments of the present disclosure.

Referring now to FIG. 4, an exemplary method 400 is shown for establishing a connectionless communication forwarding mode between a first wireless device and a neighboring wireless device of a healthcare facility, where the first wireless device may not be connected to a wireless network of the healthcare facility and the second wireless device may be connected to the wireless network. In various embodiments, one or both of the first wireless device and the second wireless device may be a wireless patient monitoring device used by a caregiver to remotely monitor a status of a patient of the healthcare facility.

As described above, the first wireless device may lose a connection to an AP to which the first wireless device is connected (also referred to herein as the connected AP). When the first wireless device loses the connection to its connected AP, the connectionless communication forwarding mode may be initiated between the first wireless device and a detected neighboring wireless device, where during the connectionless communication forwarding mode, messages directed from the first wireless device to hospital information systems or other wireless devices (e.g., a caregiver device) over the wireless network may be forwarded or relayed through the neighboring wireless device over an OOB communication channel. Method 400 is described with reference to a wireless system, such as wireless system 100 of FIG. 1 and/or hospital wireless system 200 of FIGS.

2A-2C. The first wireless device may be a non-limiting embodiment of unconnected device 152 of FIG. 1 and/or first patient monitoring device 202 of FIGS. 2A-2C. The neighboring wireless device may be a non-limiting embodiment of connected device 102 of FIG. 1 and/or second patient monitoring device 204 of FIGS. 2A-2C.

Method 400 begins at 402, where method 400 includes determining whether the first wireless device is connected to the wireless network. The first wireless device may not have been connected to the wireless network, or the first wireless device may have lost a connection to the wireless network. For example, a user (e.g., a caregiver) may move a patient connected to the first wireless device from a first location of the healthcare facility where the first wireless device is connected to an AP of the wireless network (e.g., AP 250 at first location 208) to a second location of the healthcare facility where no APs of the wireless network are available for the first wireless device to connect to.

If it is determined at 402 that the first wireless device is connected to the wireless network, method 400 proceeds to 404. At 404, method 400 includes continuing operating conditions of the first wireless device. For example, continuing operating conditions may include receiving messages and/or transmitting information to other devices and/or systems of the wireless network, such as a hospital information system, via a connected AP of the first wireless device. Method 400 may end.

If it is determined that 402 that the first wireless device is not connected to the wireless network, method 400 proceeds to 406. At 406, method 400 includes determining whether an AP of the wireless network is available for the first wireless device to connect to. If it is determined at 406 that an AP of the wireless network is available for the first wireless device to connect to, method 400 proceeds to 408. At 408, method 400 includes connecting to the available AP of the wireless network, and method 400 may end. Alternatively, if at 406 it is determined that no APs of the wireless network are available for the first wireless device to connect to, connectivity with the wireless network may not be established, and method 400 proceeds to 410.

At 410, method 400 includes delaying for hysteresis effects. In other words, method 400 may wait for a short interval to ensure that the connection to the wireless network is definitively lost. For example, the connection may be lost due to the first wireless device passing rapidly through an environment where RF signals are blocked, where upon leaving the environment, the connection may be quickly regained.

At 412, method 400 includes searching for a neighboring wireless devices of the first wireless device, via an OOB communication channel. Searching for the neighboring wireless devices via the OOB communication channel may include scanning one or more OOB communication channels for a neighboring wireless device advertising an availability of the neighboring wireless device for connectionless communication forwarding, as described above in reference to FIG. 3. For example, the first wireless device may scan the one or more OOB communication channels for a beacon transmitted by a neighboring wireless device. The beacon may be transmitted to neighboring wireless devices within a threshold distance of the first wireless device (e.g., four meters) via a low-power, short-range radio signal in a connectionless, unidirectional manner. The beacon may indicate that the OOB communication channel of the beacon is available for receiving OOB communications, or the beacon may indicate that a different OOB communication channel is available for receiving OOB communications.

At 414, method 400 includes determining whether a neighboring connected device has been detected. If at 414 it is determined that a neighboring wireless device has not been detected, method 400 proceeds to 416. At 416, method 400 may include delaying for a search interval. The search interval may be an interval during which searching for the neighboring wireless devices is paused before reinitiating a search for neighboring wireless devices at 412. For example, the search interval may range from a few seconds to a few minutes.

If at 414 it is determined that a neighboring wireless device has been detected, method 400 may proceed to 418. At 418, method 300 includes determining whether connectionless communication forwarding is allowed at the neighboring wireless device.

For example, the neighboring wireless device may not be connected to the wireless network via a Wi-Fi connection with an AP, whereby connectionless communication forwarding may not be allowed. In some embodiments, allowing connectionless communication forwarding may depend on one or more additional criteria. For example, connectionless communication forwarding may not be allowed on some types of wireless devices, or in certain situations. For example, connectionless communication forwarding may be disabled on wireless devices in the event of a security breach at the healthcare facility, or connectionless communication forwarding may not be possible due to radio interference, congestion, or other factors of an RF environment, or connectionless communication forwarding may not be possible or advisable due to a defect in a functioning of an OOB transceiver (e.g., OOB transceiver 112) of the neighboring wireless device. The neighboring wireless device may already be supporting one OOB link, or may have run out of available OOB capacity, or the neighboring wireless device may be serving a critical application where interrupting or slowing down the critical application is undesirable.

If at 418 it is determined that connectionless communication forwarding is not allowed by the neighboring wireless device, method 400 may proceed to 416, where method 400 includes delaying for the search interval prior to continuing to search for a different neighboring wireless device (e.g., a neighboring wireless device for which forwarding is allowed). Alternatively, if at 418 it is determined that connectionless communication forwarding is allowed by the neighboring wireless device, method 400 proceeds to 419.

At 419, method 400 includes initiating a connectionless communication forwarding mode between the first wireless device and the neighboring wireless device via the OOB communication channel. When the connectionless communication forwarding mode is initiated, data may be relayed from the first wireless device to devices and/or information systems of the healthcare facility connected to the wireless network by the neighboring wireless device. In various embodiments, the connectionless communication forwarding mode may be used to relay the data until the first wireless device is able to connect to a new AP of the wireless network, and resume communication of data via the wireless network.

At 420, method 400 includes waiting for an advertised connectionless communication time slot. The advertised connectionless communication time slot may be a time slot at which information may be forwarded from the first wireless device to the network. As described above in relation to method 300 of FIG. 3, each neighboring wireless device may advertise a time slot during which connectionless communication forwarding may occur via the relevant neighboring wireless device.

At 422, method 400 includes determining whether an OOB communication channel has been provided by the neighboring wireless device for the connectionless communication forwarding. In some situations, for example, in a congested RF environment with a large amount of RF interference, an OOB communication channel may not be available, or the RF environment may be challenging for establishing an OOB communication channel due to characteristics of a physical environment of the neighboring wireless device and/or the first wireless device. In some embodiments, the OOB communication channel may be the same as an OOB communication channel used by the neighboring wireless device for advertising the availability of the neighboring wireless device for connectionless communication forwarding. In other embodiments, a first OOB communication channel may be used for the advertising, and a second OOB communication channel may be used for the connectionless communication forwarding.

If at 422 it is determined that the OOB communication channel has not been provided for the connectionless communication forwarding, method 400 proceeds to 416, where method 400 includes delaying for the search interval prior to searching for a different neighboring wireless device through which information and/or messages may be forwarded.

If at 422 it is determined that an OOB communication channel has been provided by the neighboring wireless device for the connectionless communication forwarding, method 400 proceeds to 424. At 424, method 400 includes initiating a transmission of data between the first wireless device to the neighboring wireless device via connectionless communication forwarding. Transmitting data via connectionless communication forwarding may include transmitting data from the first wireless device to the wireless network via the neighboring wireless device.

As an example, a first caregiver may be treating a patient at a first location, where the first caregiver may wish to monitor a blood pressure of the patient. The patient may be connected to a hospital information system over a wireless network of the healthcare facility. When the first caregiver leaves the first location, the first caregiver may connect the patient to a wireless patient monitoring device arranged on or at the patient, and initiate a remote patient monitoring application on a first smart phone of the first caregiver. Via the remote patient monitoring application, the first caregiver may consult the blood pressure of the patient as the first caregiver leaves the patient and moves about the healthcare facility and/or as the patient moves about the healthcare facility, over the wireless network of the healthcare facility. Additionally, if the blood pressure decreases below a threshold blood pressure (e.g., relating to a treatment of the patient), the wireless patient monitoring device may generate an alert message, which may be displayed on the first smart phone of the first caregiver via the remote patient monitoring application.

Later, the patient may be moved about the healthcare facility. The patient (and the wireless patient monitoring device) may enter a second location, where connectivity to the wireless network may not be available. For example, the second location may not include an AP via which the wireless patient monitoring device can connect to the wireless network. As a result of the wireless patient monitoring device not being able to connect to the wireless network, the first caregiver may not be able to consult the blood pressure of the patient via the remote patient monitoring application. Additionally, if the blood pressure decreases below the threshold blood pressure, an alert may not be generated and displayed on the smart phone of the first caregiver. As a result of the alert not being generated and displayed on the smart phone, the first caregiver may be unaware of a change in status of the patient to which the first caregiver would otherwise respond.

Upon losing connectivity to the wireless network, the remote patient monitoring device may initiate a search for neighboring wireless devices at or near the second location. The remote patient monitoring device may scan one or more OOB communication channels for a beacon from a neighboring wireless device advertising an availability of the neighboring wireless device for connectionless communication forwarding. The remote patient monitoring device may receive a first beacon transmitted from a second smart phone of a second caregiver, indicating that the second smart phone is available for connectionless communication forwarding. The first beacon may indicate a first OOB communication channel and a time slot for the connectionless communication forwarding. In response to the remote patient monitoring device receiving the first beacon, the remote patient monitoring device may initiate a connectionless communication forwarding mode with the second smart phone, and transfer data of the patient (e.g., collected by the wireless patient monitoring device via sensors of the patient) over the first OOB communication channel.

However, the second smart phone may also be located within the second location, whereby the second smart phone may also not be connected to the wireless network of the healthcare facility. As a result of not being connected to the wireless network, the second smart phone may not be available for the connectionless communication forwarding mode, and may indicate to the wireless patient monitoring device that connectionless communication forwarding is not currently allowed by the second smart phone.

In response to the connectionless communication forwarding not being currently allowed by the second smart phone, the remote patient monitoring device may continue scanning the one or more OOB communication channels for a different neighboring wireless device advertising availability for connectionless communication forwarding. The remote patient monitoring device may receive a second beacon transmitted from a third smart phone of a third caregiver, indicating that the third smart phone is available for connectionless communication forwarding. The second beacon may indicate a second OOB communication channel and a time slot for the connectionless communication forwarding. In response to the remote patient monitoring application receiving the second beacon, the remote patient monitoring application may initiate a connectionless communication forwarding mode with the third smart phone, over the second OOB communication channel. In various embodiments, the second OOB communication channel on which the second beacon was received may be the same as the first OOB communication channel on which the first beacon was received. The third smart phone may be located outside the second location, whereby the third smart phone may also be connected to the wireless network of the healthcare facility.

When the provided time slot occurs, the wireless patient monitoring device may begin relaying patient data (e.g., blood pressure) to the third cell phone over the third OOB communication channel. The third smart phone may forward the patient data to a service of the hospital information system. The service of the hospital information system may receive the patient data. The first caregiver may then consult the blood pressure of the patient on the first cell phone, via the remote patient monitoring application. The blood pressure may be transmitted from the service of the hospital information system to the first caregiver on the first cell phone via the wireless network. When the remote patient monitoring application on the first cell phone receives the message, the blood pressure of the patient may be displayed on the first smart phone of the first caregiver. Similarly, if the blood pressure of the patient decreases below the threshold blood pressure, an alert message may be similarly generated and displayed in the remote patient monitoring application on the first smart phone. In this way, data including patient status data may be relayed between the patient and the network via the third smart phone.

The patient may then leave the second location, and move to a third location, where the wireless patient monitoring device may reconnect to the wireless network via an AP of the third location. As a result of connecting to the wireless network via the AP of the third location, the wireless patient monitoring device may terminate the connectionless communication forwarding via the third OOB channel, and resume receiving and transmitting patient data over the wireless network.

Thus, systems and methods are disclosed herein that provide an alternative connectionless messaging functionality for wireless devices of a healthcare system, using OOB radio communication, to relay data between a device that is not connected to a wireless network, and a device that is connected to the wireless network. In various embodiments, one or both of the device connected to the wireless network and the device not connected to the wireless network may be a wireless patient monitoring device. The OOB radio communication may rely on short-range, low-power radio signals, such as within a Medical Body Area Network (MBAN). By relaying the data through the device connected to the wireless network, the device not connected to the wireless network may continue to receive messages from and/or transmit information to other devices over the wireless network. By using connectionless communication forwarding when a device loses a connection to the wireless network, time-sensitive data such as patient status information, patient data, alerts, notifications, and/or other types of data may be received by the device not connected to the wireless network in a timely manner. By ensuring that the time-sensitive data is received in a timely manner, a quality of patient care may be increased and a likelihood of an undesirable outcome for a patient may be reduced.

The technical effect of using connectionless communication forwarding to relay data to and/or from a wireless device not connected to a wireless network via a device connected to the wireless network is that time-sensitive data may be communicated to the wireless device after a loss of connectivity with the wireless network.

The disclosure also provides support for a method for a patient monitoring device of a healthcare facility, comprising: initiating a connectionless communication forwarding mode with a neighboring wireless device of the patient monitoring device via out-of-band (OOB) radio communication, the patient monitoring device not connected to a wireless local area network (WLAN) of the healthcare facility and the neighboring wireless device connected to the WLAN, and while operating in the connectionless communication forwarding mode, transmitting data to an information system of the healthcare facility connected to the WLAN, the data transmitted to the neighboring wireless device via the OOB radio communication, and forwarded to the information system by the neighboring wireless device via the WLAN. In a first example of the method, the OOB radio communication includes unidirectional, short-range, low-power radio communication over an OOB communication channel. In a second example of the method, optionally including the first example, the OOB communication channel is a radio frequency channel associated with a medical body area network (MB AN). In a third example of the method, optionally including one or both of the first and second examples, the data includes a status of a patient. In a fourth example of the method, optionally including one or more or each of the first through third examples, the data includes patient data of a patient. In a fifth example of the method, optionally including one or more or each of the first through fourth examples, initiating the connectionless communication forwarding mode with the neighboring wireless device via the OOB radio communication further comprises: searching for one or more neighboring wireless devices of the patient monitoring device via the OOB radio communication, in response to connectionless communication forwarding from the detected neighboring wireless device not being allowed, continuing to search for the one or more neighboring wireless devices of the patient monitoring device via the OOB radio communication, and in response to connectionless communication forwarding from the detected neighboring wireless device being allowed, initiating the connectionless communication forwarding mode. In a sixth example of the method, optionally including one or more or each of the first through fifth examples, searching for the one or more neighboring wireless devices via the OOB radio communication further comprises receiving a beacon via the OOB radio communication from a neighboring wireless device advertising an availability for connectionless communication forwarding. In a seventh example of the method, optionally including one or more or each of the first through sixth examples, the beacon is received on a first OOB communication channel, and the beacon advertises the availability for connectionless communication forwarding via a second OOB communication channel. In a eighth example of the method, optionally including one or more or each of the first through seventh examples, the second OOB communication channel is the same as the first OOB communication channel. In a ninth example of the method, optionally including one or more or each of the first through eighth examples, advertising the availability for connectionless communication forwarding further comprises advertising a time slot during which the neighboring wireless device receives data via the OOB radio communication. In a tenth example of the method, optionally including one or more or each of the first through ninth examples, the method further comprises: in a first condition, wherein a beacon from the detected neighboring wireless device indicates that connectionless communication forwarding is not allowed, not initiating the connectionless communication mode, and in a second condition, wherein a beacon from the detected neighboring wireless device indicates that connectionless communication forwarding is allowed, initiating the connectionless communication mode.

The disclosure also provides support for a method for a wireless device connected to a wireless network of a healthcare facility, the method comprising: indicating, by transmitting a beacon from the wireless device via a first out-of-band (OOB) communication channel, an availability of the wireless device to a neighboring wireless device, for receiving information transmitted to the wireless device from the neighboring wireless device via a second OOB communication channel, and forwarding the information to an information system of the healthcare facility over the wireless network. In a first example of the method, the neighboring wireless device is not connected to the wireless network. In a second example of the method, optionally including the first example, receiving the information transmitted to the wireless device from the neighboring wireless device and forwarding the information to the information system further comprises receiving patient data transmitted to the wireless device from the neighboring wireless device and forwarding the patient data to the information system. In a third example of the method, optionally including one or both of the first and second examples, indicating the availability of the wireless device to the neighboring wireless device further comprises: in response to both of the wireless device being connected to the wireless network and connectionless communication forwarding being allowed by the wireless device, indicating the availability of the wireless device to the neighboring wireless device, and in response to either of the wireless device not being connected to the wireless network and connectionless communication forwarding not being allowed by the wireless device, not indicating the availability of the wireless device to the neighboring wireless device. In a fourth example of the method, optionally including one or more or each of the first through third examples, one or both of the first OOB communication channel and the second OOB communication channel is a radio frequency channel of a medical body area network (MBAN) within the 2360-2400 MHz band of frequencies.

The disclosure also provides support for a system, comprising: a wireless device connected to a wireless local area network (WLAN) of a hospital, the wireless device including one or more processors having executable instructions stored in a non-transitory memory that, when executed, cause the one or more processors to: indicate to a neighboring wireless patient monitoring device not connected to the WLAN, by transmitting a beacon from the wireless device via a first out-of-band (OOB) communication channel, an availability of the wireless device to initiate a connectionless communication forwarding mode with the neighboring wireless patient monitoring device via a second OOB communication channel, in response to the neighboring wireless patient monitoring device initiating the connectionless communication forwarding mode, receive data from the neighboring wireless patient monitoring device via the second OOB communication channel, and forward the received data to an information system of the hospital via the WLAN. In a first example of the system, the data includes at least one of patient data and patient status information. In a second example of the system, optionally including the first example, indicating the availability of the wireless device to the neighboring wireless patient monitoring device to initiate the connectionless communication forwarding mode via the first OOB communication channel further includes: indicating the availability of the wireless device to initiate the connectionless communication forwarding mode in response to the wireless device being connected to the WLAN and connectionless communication forwarding being allowed at the wireless device, and not indicating the availability of the wireless device to initiate the connectionless communication forwarding mode in response to at least one of the wireless device not being connected to the WLAN and connectionless communication forwarding not being allowed at the wireless device. In a third example of the system, optionally including one or both of the first and second examples, one or both of the first OOB communication channel and the second OOB communication channel is a channel of a medical body area network (MBAN).

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method comprising:

indicating, by transmitting a beacon from a wireless device of a healthcare facility via a first out-of-band (OOB) communication channel, an availability of the wireless device to a neighboring wireless device, for receiving information transmitted directly to the wireless device from the neighboring wireless device via a second OOB communication channel, the wireless device connected to a wireless network of the healthcare facility via a first access point (AP) at a first location of the healthcare facility;

detecting, at the neighboring wireless device, a loss of a connection of the neighboring wireless device to the wireless network via a second AP at a second location of the healthcare facility, the second location different from the first location;

detecting, at the neighboring wireless device, that no APs of the healthcare facility are available for the neighboring wireless device to connect to;

in response to the loss of connection and no APs being available, transmitting the information from the neighboring wireless device directly to the wireless device via the second OOB communication channel; and forwarding the information from the wireless device to an information system of the healthcare facility over the wireless network via the first AP;

wherein the wireless device is coupled to a first patient and where the neighboring wireless device is coupled to a second patient, the second patient different than the first patient.

2. The method of claim 1, wherein the wireless device is a patient monitoring device, and the information transmitted to the wireless device from the neighboring wireless device further comprises a clinical or technical alarm.

3. The method of claim 1, wherein indicating the availability of the wireless device to the neighboring wireless device further comprises:

in response to both of the wireless device being connected to the wireless network and connectionless communication forwarding being allowed by the wireless device, operating in a second mode in which the availability of the wireless device is indicated to the neighboring wireless device; and in response to either of the wireless device not being connected to the wireless network and connectionless communication forwarding not being allowed by the wireless device, operating in a first mode in which the availability of the wireless device is not indicated to the neighboring wireless device.

4. The method of claim 1, wherein the neighboring wireless device is a cell phone of a caregiver of the healthcare facility.

5. A system, comprising:

a wireless device configured to be connected to a wireless local area network (WLAN) of a hospital, the wireless device including one or more processors having executable instructions stored in a non-transitory memory that, when executed, cause the one or more processors to:

indicate to a neighboring wireless patient monitoring device not connected to the WLAN, by transmitting a beacon from the wireless device via a first out-of-band (OOB) communication channel, an availability of the wireless device to initiate a connectionless communication forwarding mode with the neighboring wireless patient monitoring device via a second OOB communication channel, wherein the wireless device transmitting the beacon via the first OB communication channel is coupled to a first patient, and wherein the neighboring wireless patient monitoring device is coupled to a second patient, the second patient different than the first patient, and wherein the wireless device is a patient monitoring device identical to the neighboring wireless patient monitoring device;

wherein the neighboring wireless patient monitoring device includes a second one or more processors having executable instructions stored in a second non-transitory memory that, when executed, cause the second one or more processors to:

detect a loss of a connection of the neighboring wireless patient monitoring device to the WLAN via a first access point (AP);

detect that no APs are available for the neighboring wireless patient monitoring device to connect to;

detect that the wireless device has initiated the connectionless communication forwarding mode; and in response to the loss of the connection of the neighboring wireless patient monitoring device, no APs being available for the neighboring wireless patient monitoring device to connect to, and the detection of the wireless device initiating the connectionless communication forwarding mode, transmit data from the neighboring wireless patient monitoring device to the wireless device via the second OOB communication channel; and wherein further instructions are stored in the non-transitory memory that when executed, cause the one or more processors of the wireless device to forward the data received from the neighboring wireless patient monitoring device to an information system of the hospital via the WLAN.

6. The system of claim 5, wherein the data includes at least one of patient data and patient status information.

7. The system of claim 6, wherein the indicating the availability of the wireless device to the neighboring wireless patient monitoring device to initiate the connectionless communication forwarding mode via the first OB communication channel further includes:

operating in a second mode in which the availability of the wireless device to initiate the connectionless communication forwarding mode is indicated in response to the wireless device being connected to the WLAN and connectionless communication forwarding being allowed at the wireless device; and operating in a first mode in which the availability of the wireless device to initiate the connectionless communication forwarding mode is not indicated in response to at least one of the wireless device not being connected to the WLAN and connectionless communication forwarding not being allowed at the wireless device.

8. The system of claim 7, wherein one or both of the first OOB communication channel and the second OOB communication channel is a channel of a medical body area network (MBAN).

* * * * *